United States Patent
Sarrine

(10) Patent No.: US 6,451,263 B1
(45) Date of Patent: Sep. 17, 2002

(54) PIPETTE ADAPTER

(75) Inventor: Robert James Sarrine, Beaumont, TX (US)

(73) Assignee: Helena Laboratories Corporation, Beaumont, TX (US)

( * ) Notice: Subject to any disclaimer, the term of this patent is extended or adjusted under 35 U.S.C. 154(b) by 0 days.

(21) Appl. No.: 09/433,962

(22) Filed: Nov. 4, 1999

(51) Int. Cl.7 .................................................. B01L 3/02
(52) U.S. Cl. .................. 422/100; 73/863.32; 73/864.12
(58) Field of Search ....................... 422/100; 73/864.12, 73/863.32

(56) References Cited

U.S. PATENT DOCUMENTS

| | | | |
|---|---|---|---|
| 3,581,575 A | * | 6/1971 | Butler |
| 4,215,092 A | * | 7/1980 | Suovaniemi et al. |
| 4,734,261 A | * | 3/1988 | Koizumi et al. |
| 4,779,467 A | * | 10/1988 | Rainin et al. |
| 4,801,434 A | * | 1/1989 | Kido et al. |
| 5,057,281 A | * | 10/1991 | Torti et al. |
| 5,061,449 A | * | 10/1991 | Torti et al. |
| 5,335,481 A | | 8/1994 | Ward |
| 6,235,244 B1 | * | 5/2001 | Allen et al. .................. 422/100 |

FOREIGN PATENT DOCUMENTS

DE       197 12 195 A       9/1998

* cited by examiner

*Primary Examiner*—Jill Warden
*Assistant Examiner*—Brian Sines
(74) *Attorney, Agent, or Firm*—Piper Rudnick LLP; Jerold I. Schneider

(57) ABSTRACT

A multichannel pipette has downwardly depending tip cones to receive disposable tips which have free ends. Adjacent tip cones, and thus the disposable tips, are spaced apart a first distance, which is referred to as the intra-channel spacing. An adapter changes the intra-channel spacing of the free ends of the pipette tips. The adapter has a series of apertures therethrough, and the distance (center-to-center) between adjacent apertures differs from the first distance. The disposable tips are inserted through the adapter to change the intra-channel spacing between the free ends of the tips, either by spreading out or contracting the spacing between the free ends of the tips.

6 Claims, 2 Drawing Sheets

PIPETTE ADAPTER

BACKGROUND ART

This invention relates to pipette applicator devices and has particular utility in connection with antisera applicators in an immunofixation electrophoresis system wherein a standard multi-channel pipette has intra-channel spacing which is inconsistent with the spacing needed for the applicators.

Immunofixation electrophoresis, referred to as IFE, is well-known as a two-stage procedure for detecting the presence of certain proteins in human serum, urine or cerebral spinal fluid. The procedure involves, as a first step, protein fraction resolution by electrophoresis. As a second step, the soluble antigen in each protein fraction is allowed to react with its antibody. The resultant antigen-antibody complexes will precipitate, at a rate dependent upon the proportion of the reactants, temperature, salt concentration and pH. The antigen-antibody complexes are then visualized by staining.

The IFE process is described in greater detail in Gebott et al., U.S. Pat. No. 4,668,363 issued May 26, 1987, which is hereby incorporated by reference. Apparatus and chemicals for performing IFE have been marketed for some time by Helena Laboratories Corporation of Beaumont, Tex.

Typically, a specimen from a single patient is diluted and then placed in multiple sample or application areas (also referred to as zones or lanes) on a single electrophoretic gel plate. The purpose of utilizing multiple sample areas is to enable detection separately of total serum protein, and various proteins such as the immunoglobin heavy chains IgG, IgM, IgA and light chains Kappa and Lambda, or other proteins whose presence or absence may be of importance in medical diagnosis. As known in the prior art, various antisera (i.e., fluid containing the antibody) such as IgG, IgM, etc., are deposited on the appropriate zones or lanes and permitted to react with the antigen in the sample. The term "incubation" refers to the time interval during which the antisera and antibody are in contact such that a reaction may occur.

U.S. Pat. No. 5,137,614, issued on Aug. 11, 1992 to Golias, which is hereby incorporated by reference, is directed to a control system for verifying the effectiveness of the chemicals utilized in the immunofixation electrophoresis procedure. This is accomplished without the need to interrupt patient specimen evaluation when chemicals are replenished, since the chemical utilized on the specimens are also utilized in the control test. The control system verifies that the chemicals have retained their lability.

U.S. Pat. No. 3,844,918, issued on Oct. 29, 1974 to Crawley, which is hereby incorporated by reference, is directed to a template which includes an aperture through which serum is received. The template is placed on a mold having an extended portion which passes through the aperture. Gel is coated on one surface of the template. When the gel molds around the portion extending through the aperture, the mold is removed from the template. The template is left with a small cavity in which the serum is placed.

U.S. Pat. No. 5,403,456, issued on Apr. 4, 1995 to Bellon, which is hereby incorporated by reference, is directed to a mask which includes an orifice through which liquid is deposited on the zone of the gel, and a slit through which excess liquid is withdrawn from the zone of the gel after the incubation step. In practice, the mask is placed in close proximity to, but spaced apart from the surface of the gel, the liquid is deposited through the mask onto the gel, the mask is maintained in its relative position during the incubation step, and, thereafter, excess liquid is withdrawn through the mask. Then, of course, the mask, is removed.

It is preferred, for reasons of economy, to evaluate samples of multiple patients simultaneously. This has been accomplished, in the past, using multiple "sets" or groups of zones on a single electrophoresis gel. Thus, if six zones are required for the desired analysis for a single patient, and if the samples from as many as six patients are to be evaluated simultaneously, then 6×6 or 36 zones or lanes are used on the electrophoresis gel. As would be expected, after the electrophoresis step, the appropriate antisera must be applied to the corresponding zone for each patient. For example, if blood samples of six patients are being evaluated simultaneously, then after the electrophoresis step, one antisera (e.g., IgG antisera) was applied sequentially to the corresponding zone for each patient using a pipette of the type which has a removable, disposable tip. Then, the tip on the pipette would be removed, and another antisera (e.g., IgM antisera) would be applied sequentially to the corresponding zone for each patient using a second disposable tip. This procedure would be repeated for each of the antisera. Of course, it was possible to apply the various antisera to the corresponding zones for a single patient, and then repeat the process for the next patient, etc., but this would be cumbersome, time consuming, and create a potential for errors because of the large number of pipette tips which would be used, i.e., 36 tips.

As a first improvement on the processing of samples from multiple patients simultaneously, Helena Laboratories Corporation, assignee of the present invention, developed and marketed a system in which samples from as many as six patients, i.e., 36 zones, can be processed simultaneously using, inter alia, a multiple channel pipette for dispensing the six antisera simultaneously onto the six lanes representing a single patient. Then, the pipette is "reloaded" and antisera dispensed onto the six lanes representing the second patient, etc.

The desire to increase productivity and thus reduce the cost per "test" has resulted in the modification of the electrophoresis gel to accomodate samples from nine patients, i.e., 54 zones. However, since automatic electrophoresis equipment, such as the equipment marketed by Helena Laboratories Corporation under the trademark REP® already exists, it is not practical to change the size of the electrophoresis gel plate, notwithstanding that 54 zones instead of 36 zones are present. Thus, it should be appreciated that while the overall size of the gel has not changed, the spacing between zones on the gel has changed.

Applicant has discovered, however, that while the electrophoresis equipment manufactured by Helena Laboratories Corporation can process 54 zones simultaneously, there are no multiple channel pipettes which can be used to simultaneously dispense the six antisera on the six zones or lanes corresponding to a single patient, when a 54 zone (i.e., 9 patients) gel is used. Furthermore, the demand for specially designed multiple channel pipettes for the above purpose and the resulting cost is not justified by the quantity of electrophoresis machines involved, even though a large number of tests per se are performed each year. In other words, there is not a suffient number of hospitals and independent laboratories to support a custom-made multiple channel pipette which is dimensioned for 9 patient gel.

SUMMARY OF THE INVENTION

The present invention overcomes the difficulties and shortcomings of the prior art by which providing an adapter which may be used on a standard, multiple channel pipette, and which changes the spacing between the replaceable tips, by spreading (or contracting, if necessary) the spacing between the cones of the pipette onto which each removable tip is placed.

BRIEF DESCRIPTION OF DRAWINGS

The various objects, advantages and benefits of the present invention will become more apparent upon reading the following detailed description of the invention taken in conjunction with the drawings. In the drawings.

DISCLOSURE OF THE INVENTION

The present invention is described in the non-limiting but merely illustrative context of an adapter for a multiple channel or multiple sample pipette for use in immunofixation electrophoresis. In this regard, it should be appreciated that the principles of the present invention may be utilized to modify the intra-channel spacing of a multi-channel pipette, regardless of whether the pipette will be used in the IFE process.

Figure 1:
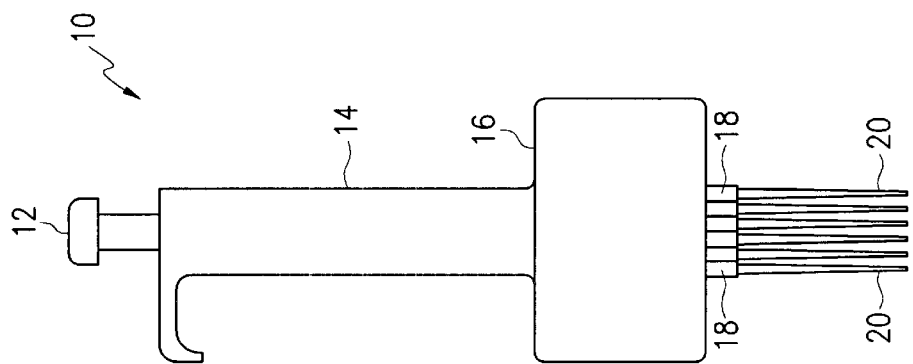
FIG. 1 is a view of a multiple channel or multiple sample pipette according to the prior art.
Figure 3:
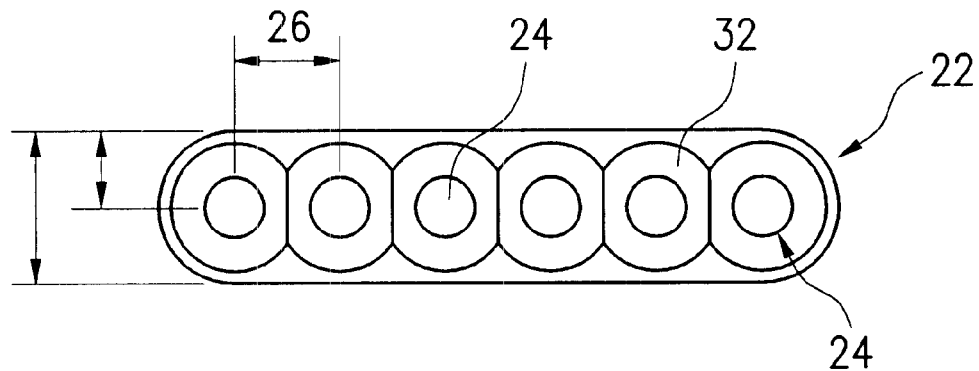
FIG. 3 is a plan view of the adapter according to the present invention.
Figure 4:
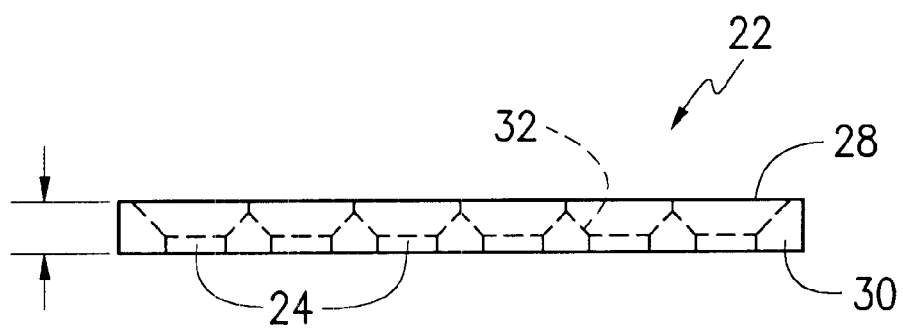
FIG. 4 is a front elevation of the adapter of FIG. 3.

With reference to the drawings, a conventional multi-channel pipette 10 is illustrated in FIG. 1. As noted previously, when utilizing an electrophoresis gel plate having 54 zones, the center-to-center distance between adjacent lanes for the same patient are approximately 0.264 inches, and there is no "standard" multiple channel pipette, with 0.264 spacing between the adjacent lanes or zones, such that the six antisera can be simultaneously applied to the six zones corresponding to a single patient. A prior art pipette 10, identified, for purpose of explanation and not limitation, as a Model 384 Multichannel Pipette manufactured by Labsystems of Helsinki, Finland, has an operating button 12, a handle 14, a body 16, and six "tip cones" 18 extending downwardly from the body 16. The pipette just described, as initially manufactured, has at least 12 channels (i.e., 12 tip cones) and it is intended that tip cones may be removed and the intra-channel spacing adjusted. In use, replaceable conical, hollow tips 20 are placed on the tip cones as is conventional, the tips are placed into the fluid to be dispensed, fluid is drawn into the tips, the pipette is moved to be aligned over the lanes where the fluid is to be dispensed, and the button 12 operated to dispense the fluid. However, this prior art pipette can not be used in the desired application because the intra-lane spacing of the tip cones, and thus the removable tips, differs from the intra-lane spacing of the samples on the gel.

Figure 2:
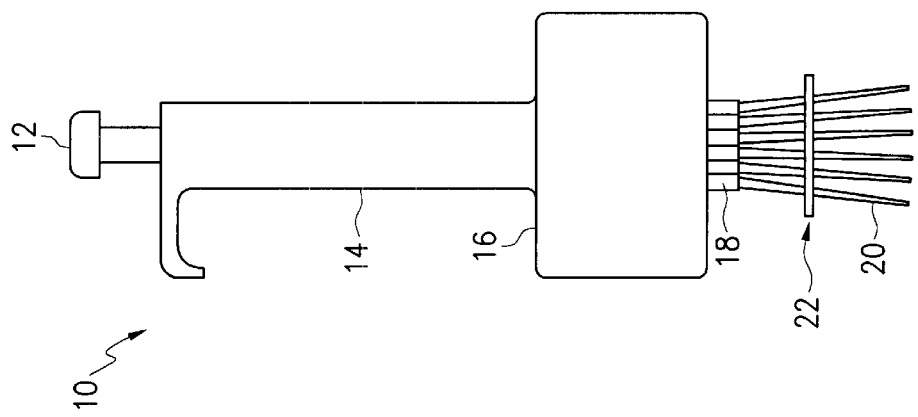
FIG. 2 is a view of a multiple channel or multiple sample pipette including an adapter according to the present invention.

Since it is desired to use only six channels, the pipette 10 is modified so that only six tip cones remain and, for this purpose, only six tip cones and six tips are illustrated in each of FIGS. 1 and 2.

According to the principles of the present invention an adapter 22, which may be made of crystal styrene, is provided to modify the intra-channel spacing. The adapter 22 is a thin, elongated member having six apertures 24 therethrough. In a non-limiting explanation of the relative dimensions, the center-to-center distance 26 between adjacent apertures may be 0.210 inches. The adapter has first and second surfaces 28, 30, and the aperture diameter is 0.118 inches. Each aperture is countersunk or chamfered 32 from the first surface 28 at a diameter of 0.25 inches.

The use of the adapter of the present invention will now be explained. In the immunofixation electrophoresis environment, using the prior Helena Laboratories Corporation apparatus for simultaneously applying all six antisera to all six zones on an electrophoresis gel corresponding to a single patient, (where the gel has the capacity for simultaneous processing of samples for as many as six patients) the pipette is inserted into a rack containing an array of tips 20, such that the cones 18 are pushed into, and frictionally retain, the tips 20. Then the pipette, with the tips on the cones, is moved from the rack containing an array of tips, and the tips inserted into the antisera. Thereafter, the pipette was actuated to fill the tips and then moved to the electrophoresis gel with the tips aligned over the zones or lanes corresponding to a single patient, whereupon the antisera were simultaneously dispensed (through a template) onto the six lanes corresponding to the single patient.

However, the intra-channel spacing of the tip cones 18 and tips 20 does not permit use with a 9 patient gel. Thus, in the present invention, after the cones are inserted into the tips, the adapter 22 is placed over the tips, to spread the tips to the configuration illustrated in FIG. 2. Thus, the tips spread outwardly similar in appearance to the tines on a rake. The chamfer or countersink limits the distance that the adapter slides along the tips toward the body 16. Furthermore, the use of a chamfer or countersink 32 permits the various tips 20 to be inserted into the corresponding apertures 24 without first manually spreading apart the tips. The countersink or chamfer 32 is such that adapter moves upwardly on the tips a predetermined distance, resulting in the desired intra-tip spacing of 0.264 inches at the free end of the tips. Thereafter, the tips are inserted into the antisera, filled and then moved to the location of the electrophoresis gel, such that the six antisera may be simultaneously deposited on the six zones corresponding to a single patient.

It should be appreciated that, as illustrated, the adapter is used to expand the intratip distance. However, if the initial intra-lane spacing of the tip cones 18 is too large, the adapter of the present invention may be used to reduce the intra-tip spacing.

The foregoing is a description of the present invention. Many changes and modifications may be made without departing from the spirit and scope of the present invention. The present invention, therefore, should be limited only by the following claims.

What is claimed is:

1. A method for adjusting the intra-channel spacing of a multichannel pipette of the type having a plurality of tip cones, spaced apart a first distance, comprising:

provide a plurality of hollow pipette tips each having a first end and a free end;

establishing a fluid flow path between each tip cone and a corresponding pipette tip at the pipette tip first end; and placing an adapter on the pipette tips, the adapter having a plurality of apertures, the pipette tips extending through said apertures for changing the spacing between the free ends of adjacent pipette tips without changing said first distance.

2. The method as defined in claim 1 wherein the adapter is placed onto the pipette tips after the tip cones are inserted into the pipette tips.

3. The method as defined in claim 1 wherein the spacing between the free ends of the pipette tip is increased.

4. The method as defined in claim 1 wherein the apertures in said adapter are spaced apart a second distance different from said first distance.

5. The method as defined in claim 1 wherein the adapter is frictionally retained on said pipette tips.

6. The method as defined in claim 1 wherein the distance between adjacent pipette tips changes along the length of the pipette tips.

* * * * *